United States Patent
Kuvshinov et al.

(12)

(10) Patent No.: US 6,455,761 B1
(45) Date of Patent: Sep. 24, 2002

(54) AGROBACTERIUM-MEDIATED TRANSFORMATION OF TURNIP RAPE

(75) Inventors: Viktor Kuvshinov, Vantaa; Kimmo Koivu, Helsinki; Anne Kanerva, Helsinki; Eija Pehu, Helsinki, all of (FI)

(73) Assignee: Helsinki University Licensing Ltd. Oy, Helsinki (FI)

( * ) Notice: Subject to any disclaimer, the term of this patent is extended or adjusted under 35 U.S.C. 154(b) by 0 days.

(21) Appl. No.: 09/508,371

(22) PCT Filed: Sep. 16, 1998

(86) PCT No.: PCT/FI98/00730

§ 371 (c)(1), (2), (4) Date: Mar. 10, 2000

(87) PCT Pub. No.: WO99/14349

PCT Pub. Date: Mar. 25, 1999

(30) Foreign Application Priority Data

Sep. 18, 1997 (FI) .................................................. 973720

(51) Int. Cl.$^7$ ........................ C12N 15/82; C12N 15/84; A01H 4/00
(52) U.S. Cl. ....................... 800/294; 800/278; 800/306; 435/468; 435/469; 435/431; 435/430.1
(58) Field of Search ................................ 435/468, 469, 435/431, 430.1; 800/278, 294, 306

(56) References Cited

U.S. PATENT DOCUMENTS

| | | | | |
|---|---|---|---|---|
| 4,672,035 A | 6/1987 | Davidonis et al. | ........... | 435/427 |
| 5,188,958 A | 2/1993 | Moloney et al. | ............ | 800/300 |
| 5,463,174 A | 10/1995 | Moloney et al. | ............ | 800/294 |
| 5,633,435 A | 5/1997 | Barry et al. | ................ | 800/288 |

FOREIGN PATENT DOCUMENTS

WO 98 00557 1/1998

OTHER PUBLICATIONS

Enriquez–Obregon et al., "Genetic Transformation of Sugarcane by *Agrobacterium tumefaciens* Using Antioxidant Compounds." 1997, Biotecnologia Aplicada, vol. 14, pp. 169*174.*

Block, et al., "Transformation of *Brassica napus* and *Brassica oleracea* Using *Agrobacterium tumefaciens* and the Expressions of the bar and neo Genes in the Transgenic Plants." 1989, Plant Physiol., vol. 91, pp. 694–701.*

Thomzik, J. "Agrobacterium–Mediated Transformation of Stem Disks from Oilseed Tape (*Brassica napus* L.)" 1995, Methods in Molecular Biology, vol. 44, 99–79–85.*

Chi, Gek–lan et al., "Effect of AgNO3 and aminoethoxyvinylglycine on it vitro shoot and root organogenesis from seedling explants of recalcitrant Brassica genotypes", Plant Cell Reports (1990) 9: pp. 195–198.

Fry, Joyce, "Transformation of *Brassica napus* with *Agrobacterium tumefaciens* based vectors", Plant Cell Reports (1987) 6: pp. 321–325.

Hachey, John E. et al., "Efficient shoot regeneration of *Brassica campestris* using cotyledon explants cultured in vitro", Plant Cell Reports (1991) 9: pp. 549–554.

Knutzon, Deborah S. et al., "Modification of Brassica seed oil by antisense expansion of a stearoyl–acyl carrier protein desaturase gene", Proc.Natl.Acad.Sci. USA, vol. 89, pp. 2624–2628, Apr. 1992.

Palmer, C.E., "Enhanced shoot regeneration from *Brassica campestris* by silver nitrate", Plant Cell Reports (1992) 11: pp. 541–545.

Shiba, Hiroshi et al., "Breakdown of Self–incompatibility in Brassica by the Antisense RNA of the SLG Gene", Proc. Japan Acad., vol. 71, Ser. B. (1995) pp. 81–83.

Radke Sharon E. et al,: Plant Cell Reports, 11 (10):p499–505 1992.

Answer 30 of 221 Biosis Copyright 1998 97–339151, Takasaki T. et al Abstract Only.

Plant Cell Reports (1992) 11:506–513, A. Mukhopadhyay et al.

Plant Cell Reports (1987) 6:321–325, Joyce Fry et al.

* cited by examiner

*Primary Examiner*—David T. Fox
*Assistant Examiner*—David H Kruse
(74) *Attorney, Agent, or Firm*—Birch, Stewart, Kolasch & Birch, LLP

(57) ABSTRACT

The present invention relates to plant biotechnology and specifically to a novel transformation protocol for obtaining transgenic turnip rape plants with Agrobacterium mediated transformation. In the protocol an internode section of the inflorescence carrying stem of mature turnip rape is used as explant.

15 Claims, 2 Drawing Sheets

AGROBACTERIUM-MEDIATED TRANSFORMATION OF TURNIP RAPE

This application is the national phase under 35 U.S.C. §371 of PCT International Application No. PCT/JP98/00730 which has an International filing date of Sep. 16, 1998, which designated the United States of America.

FIELD OF THE INVENTION

The present invention relates to plant biotechnology and specifically to a novel transformation protocol for obtaining transgenic turnip rape plants.

BACKGROUND OF THE INVENTION

Turnip rape (*Brassica rapa* ssp. *oleifera*, syn. *B. campestris*) is general oil producer crop in the Northern Europe, Canada and Indian subcontinent. Canola type turnip rape oil has a high nutritional quality. Seeds of turnip rape are rich in storage proteins, which enables there usage as forage. Due to high industrial importance, turnip rape is often involved in transgenic investigations. However, there are not many reports about successful genetic transformation of the plant.

Transformation protocols using Agrobacterium infection have been developed for hypocotyl explants of turnip rape, *B. rapa* ssp. *oleifera* (Radke et al. 1992) and brown sarson, *B. campestris* (Mukhopadhyay et al. 1992). Some other reports on Agrobacterium mediated transformation of turnip rape (Knutzon et al. 1992; Shiba et al. 1995) are based on the protocol of Radke et al. 1992 (supra). Shoot regeneration on turnip rape explants has been very problematic and was the main obstacle which delayed development of transformation protocols in the 1980's. Recently, recalcitrancy of *B. rapa* ssp. *oleifera* was overcome by using silver nitrate in the cultural medium during shoot regeneration of hypocotyl and cotyledon explants (Chi et al. 1990; Hachey et al. 1991; Palmer 1992).

Transformation protocols for explants of mature plants of a close relative of turnip rape, namely oilseed rape (*Brassica napus*), have been successfully developed (Fry et al. 1987; Pua et al. 1987; Radke et al. 1987). U.S. Pat. No. 5,188,958 for Moloney and Radke claims transformation of Brassica species. In the specification successful transformation has been shown for *Brassica napus* (cv. Westar) only.

SUMMARY OF THE INVENTION

Our specific aim is to use mature plant tissue, especially inflorescence carrying stem segments as an explant source enabling us to successfully propagate and transform the same plant genotype. In preliminary experiments we have examined different factors, which could have an effect on regeneration and transformation capacities of different explants of a mature plant. As a result of the experiments we have developed a new transformation protocol for inflorescence carrying stem segments of mature turnip rape plants using *Agrobacterium tumefaciens* infection.

The present invention thus provides a new and efficient transformation protocol of mature plants of turnip rape, in which protocol an internode section of the inflorescence carrying stem of a mature turnip rape plant is excised, the section is sterilized and cut into segments, which are then placed in a horizontal position on an agar cultivation medium (MS-medium) which is supplemented with silver nitrate and a hormone. Sucrose is used in all MS culturing media. The segments are cultivated on said medium for 1 day (24 hours) and then immersed in a MS solution inoculated with *Agrobacterium tumefaciens* bacteria carrying at least one gene foreign to said turnip rape. The extra liquid on the immersed segments is removed with a filter paper and the explants are placed in a horizontal position on a MS agar co-cultivation medium supplemented with hormones and optionally with acetosyringone, and co-cultivated with Agrobacteria for 2 days (48 hours) so as the transformation to be effected. The co-cultivated segments are then washed from the Agrobacteria and placed immediately in a vertical position with the basal side down on MS agar for selection with antibiotics. Selection is carried out for 3 to 6 weeks using kanamycin or hygromycin. Subsequently the stem segments are placed on a regeneration medium supplemented with hormones, and the transgenic shoots regenerated are separated, and grown for about 1 month on a MS medium without hormones. The main steps of the transformation protocol of the invention are given in FIG. 1.

DETAILED DESCRIPTION OF THE INVENTION

Figure 1:
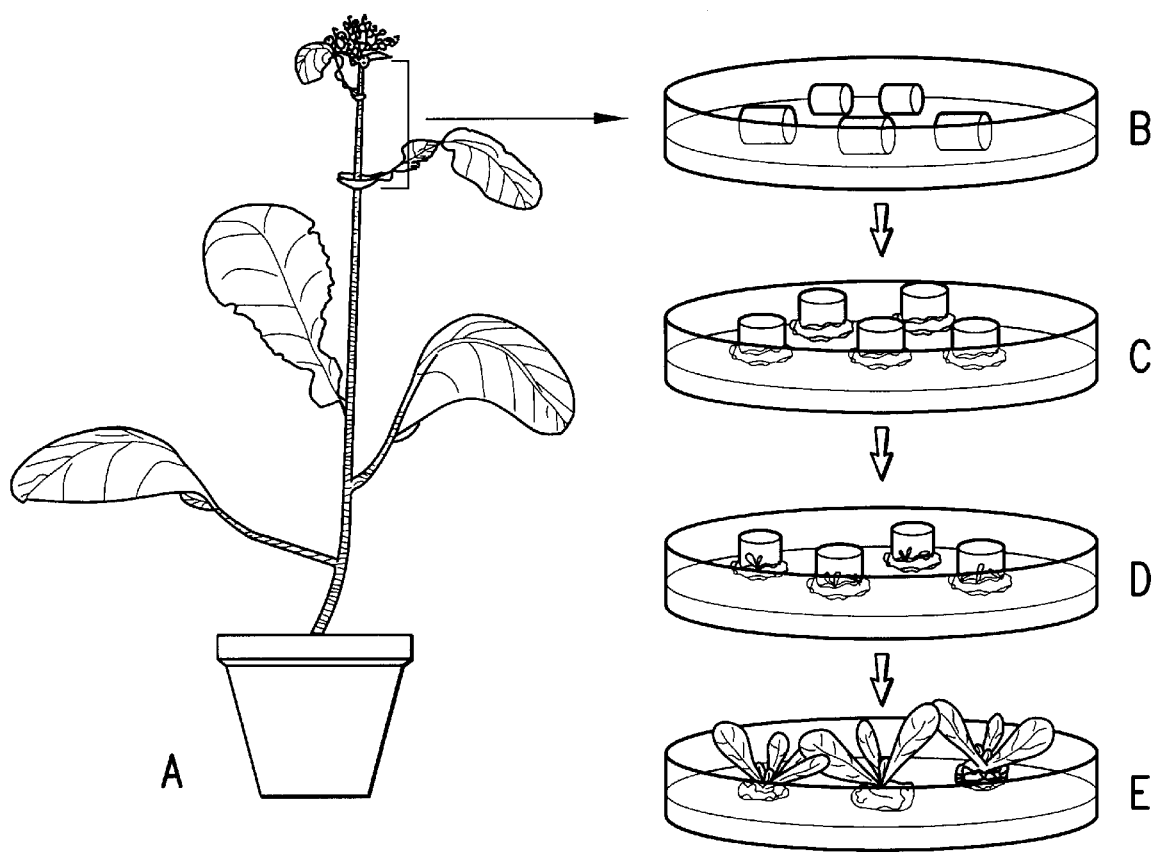
FIGS. 1A–1E show the steps of the transformation protocol of the invention. A. Plant—donor of explants for transformation. Upper one-two internodes are marked. B. Stem segments used for transformation are placed in a horizontal position. C. After co-cultivation the stem segments are placed on MS agar for selection, in a vertical position basal side down. D. and E. Shoots regenerated in the first month are separated and grown without hormones.

Inevitable prepositions for successful transformation of turnip rape stem explants are the following:

A good growth status of greenhouse plants used for transformation. Plants should grow fast, be green and be free of contamination. When taking the stem explant, the plants should be in a certain growth stage, i.e. just before the stage of inflorescence elongation before opening of the first flowers.

The stem explants are excised from upper 2–5 cm long one-two internodes, sterilized and used in transformation.

The internodes are cut in 4–8 mm segments and placed on MS agar in horizontal position for a pre-cultivation step (one day) and subsequently for a co-cultivation step with *Agrobacterium tumefaciens* (two days).

After three days the explants are washed to remove Agrobacteria and situated in a vertical position (basal side down) on MS agar for selection, as the regeneration of shoots mainly happens on the basal sides of stem segments.

Selection of transformed tissues should be started immediately after co-cultivation.

Hormone treatment at different culturing stages is dependent on the cultivar used but varies within the following ranges:

3–6 days of 0.5–3 mg/l 2,4-D>>1–2 weeks of 2–3 mg/l BAP and 0–0.1 mg/l NAA>>separation of regenerated shoots>>1 month without hormones>>rooting on 0–0.5 mg/l NAA.

15–90 μM (2.5–15 mg/l) of silver nitrate in MS medium as well as porous paper tape for sealing of plates are required for decreasing ethylene content in plates with explants and intensive aeration thereof, both during transformation and selection/regeneration.

Experimental

Abbreviations

| | |
|---|---|
| BAP | 6-benzylaminopurine |
| 2,4-D | 2,4-dichlorophenoxyacetic acid |
| GUS | β-glucuronidase (uidA reporter gene) |
| Hyg | Hygromycin |
| IAA | indole-3-acetic acid |
| Kan | Kanamycin |
| MS | Murashige-Skoog medium or agar |
| NAA | α-naphthaleneacetic acid |
| YEB | Medium for cultivation of Agrobacterium cells |

Composition of Murashige-Skoog (MS) plant growth medium:

| Salts: | | Vitamins: | |
|---|---|---|---|
| | g/l | | mg/l |
| $NH_4NO_3$ | 1.65 | Thiamine | 0.1 |
| $KNO_3$ | 1.9 | Pyridoxine | 0.1 |
| $MgSO_4 \times 7H_2O$ | 0.37 | Nicotinic acid | 0.5 |
| $KH_2PO_4$ | 0.17 | Myo-inositol | 100 |
| $CaCl_2 \times 2H_2O$ | 0.44 | Glycine | 2.0 |
| | mg/l | | g/l |
| $H_3BO_3$ | 6.2 | Sucrose | 2.0 |
| $MnSO_4 \times 4H_2O$ | 22.3 | Agar | 7 |
| $ZnSO_4 \times 7H_2O$ | 8.6 | pH 5.6 | |
| KJ | 0.83 | | |
| $Na_2MoO_4 \times 2H_2O$ | 0.25 | | |
| $CuSO_4 \times 5H_2O$ | 0.025 | | |
| $CoCl_2 \times 2H_2O$ | 0.025 | | |

Materials and methods:

Plant material. Seeds of Finnish turnip rape cultivars Valtti and Sisu were germinated and grown for 3–4 weeks under greenhouse conditions. In the stage of stem elongation, before opening of the first flowers, upper 2–5 cm long 1–2 internodes of the inflorescence carrying stem were excised and sterilized for 90 sec. in 70% ethanol and 10 min. in Na-hypochlorite (2% of active Cl⁻) with addition of Tween-20, and washed 3 times in sterile water. Then the internode section was cut into 4–8 mm long segments which were used for transformation.

*Agrobacterium tumefaciens* strains C58C1 which harbored pGV3850 (Zambryski et al.1983), C58C1 which harbored pGV2260 (Deblaere et al. 1985), EHA105 (Hood et al. 1993) and LBA4404 which harbored pAL4404 (Hoekema et al. 1983) were tested on transformation of turnip rape. UidA (GUS) gene containing an intron (uidA-int) (Vancanneyt et al. 1990) was cloned into all T-region containing vectors as listed above and used in transformation. This gene construction which contains an intron prevents GUS expression in bacteria and enables to detect plant transformation events at an early stage. Cointegrative pHTT294 vector essentially similar to pHTT370 (Elomaa et al. 1993) carrying uidA gene with intron, under 35:35S-AMV promoter (Datla et al. 1993) was used for transformation in C58C1 strains. The uida gene was removed from binary pGPTV-KAN and pGPTV-HPT vectors (Becker et al. 1992) and replaced with uida gene containing an intron, fused with CaMV 35S promoter. The vectors obtained were transformed into all of the above mentioned strains.

Agrobacteria were grown overnight with shaking in liquid YEB medium (Lihtenstain and Draper, 1985) supplemented with appropriate antibiotics. Subsequently, 1/100 v/v aliquot was inoculated in the fresh YEB (the same antibiotics) with or without 100 μM acetosyringone and then bacteria were grown over another night with shaking. Agrobacterium culture $OD_{600}=1.0$ was used in transformation.

Plant transformation. Turnip rape inflorescence carrying stem explants (4–8 mm long) were cultivated for 24 hours in horizontal position on 0.7% MS agar medium (Murashige and Skoog, 1962) supplemented with silver nitrate. 2–3% sucrose was used in all MS culturing media, and all in vitro culturing was performed in 16 h daylight at 25° C. and 18° C. day/night temperatures. Then the explants were immersed for 1–3 min. in MS solution inoculated with a dilution (e.g. 1/10 v/v) of the overnight culture of *Agrobacterium tumefaciens*. Thereafter extra liquid on the stem segments was removed using filter paper and the explants were placed horizontally on MS agar for co-cultivation with bacteria for 2 days. The medium was supplemented with acetosyringone (3,5-dimethoxy-4-hydroxyacetophenon (Aldrich)) and hormones. The explants were washed in water solution (700 mg/l) of claforan (cefotaxim), or carbenicillin. Then the surfaces of the explants were dried on filter paper and the explants were placed vertically, basal side down on medium for selection.

Selection and regeneration. Eventually, cultivation of the explants for 3–6 days on 0.5–1.5 mg/l 2,4-D and then for 7–14 days on 2–3 mg/l BAP and 0–0.05 mg/l NAA (concentrations and time depending on plant cultivar) was found as the best for green embryogenic nodules and primordia formation. Thereafter the whole explants or cut callus pieces with the green nodules and primordia were transferred on hormone free MS medium, where nodules developed primordia and shoots. Silver nitrate in concentration 0–90 μM (0–15 mg/l) and porous paper tape for sealing of Petri dishes were used in transformation and regeneration of transgenic plants.

Recovered transgenic shoots were grown on hormone free MS medium or supplemented with 0.1–0.2 mg/l NAA for stimulation of rooting, stem elongation, micropropagation and prevention of inflorescence formation.

Selection on kanamycin or hygromycin was applied immediately after co-cultivation of the explants with Agrobacteria, three days after beginning of the whole procedure. Antibiotics were used in concentrations 20–25 mg/l during all steps of regeneration and cultivation of transgenic plants.

Analysis of transgene expression. Histological GUS assay was performed on transformed callus and leaf tissue. We used for plant transformation only an uida gene version which contains an intron to prevent GUS expression in Agrobacteria. It enables us to test GUS activity in early stages of transformation even immediately after co-cultivation. Usually we made a GUS assay 4 days after co-cultivation with Agrobacteria in optimization experiments.

The following Table 1 shows the preferred conditions for the transformation of cultivars Sisu and Valtti in the present transformation procedure.

TABLE 1

|  |  | Pre-cultiv. 1 day | Co-cultiv. 2 days | Selection 1–2 weeks | Selection 2–4 weeks | Rooting |
|---|---|---|---|---|---|---|
| Sisu | Hormones | 1.5 mg/l 2, 4-D | 1.5 mg/l 2, 4-D | 3 mg/l BAP + 0.005 mg/l NAA | without | 0.2 mg/l NAA |
|  | Silver nitrate | 30 µM | 0–30 µM | 30 µM | 30 µM | 15 µM |
|  | Selection | — | — | 20 mg/l Kan/Hyg | 20 mg/l Kan/Hyg |  |
| Valtti | Hormones | 0.5 mg/1 2, 4-D | 0.5 mg/l 2, 4-D | 3 days 0.5 mg/l 2, 4-D -)-) 3 mg/l BAP + 0.05 mg/l NAA (or 2 mg/l BAP) | without | 0.2 mg/l NAA |
|  | Silver nitrate | 30 µM | 0–30 µM | 30 µM | 30 µM | 15 µM |
|  | Selection | — | — | 25 Kan, 20 Hyg | 20–25 Kan/Hyg |  |

Transgenic plants which showed steady positive GUS expression and grew well under selection conditions were grown in a greenhouse and used for Southern blot analysis to confirm transformation events on DNA level and to estimate quantity of transgene insertions in the plant genome.

Southern Analysis

Figure 2:
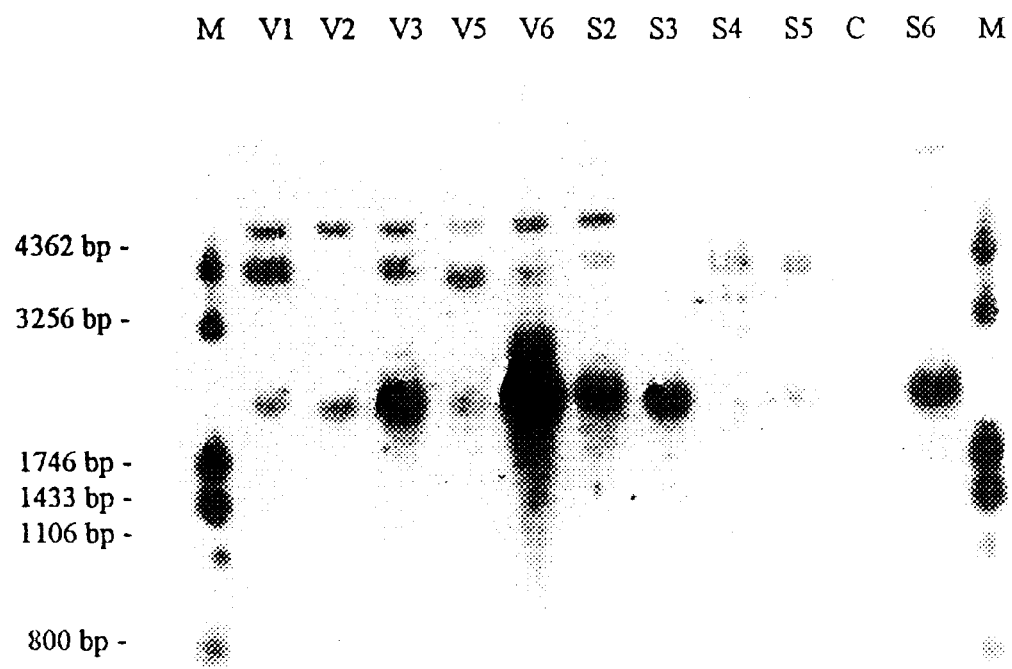
FIG. 2 shows the result of Southern blot analysis of transgenic lines of turnip rape cultivars Valtti and Sisu. Abbreviations: M—molecular weight marker; V1–V6—transgenic lines of cv. Valtti; S2–S6—transgenic lines of cv. Sisu; C—negative control (=DNA of non-transformed turnip rape plant). Plant DNA samples were digested with EcoRI and BamHI restriction enzymes.

Southern analysis was performed using digoxigenin PCR labeled uidA gene probe according to the protocol developed by Boehringer Mannheim. 3 pg of DNA from GUS positive turnip rape plants was digested with EcoRI and BamHI restriction enzymes. These enzymes cut out a 2 kb uidA gene fragment from the T-region of PGPTV-KAN (-HPT) inserted in the plant genome. As the T-region contains a further BamHI restriction site, and because of incomplete restriction of plant DNA preparations there were 6 kb and 4 kb positive bands in some of the tracks. A typical Southern blot is given in FIG. 2. Transgenic lines V2, V5 and V6 of cv. Valtti and S5 of cv. Sisu were transformed using pGPTV-KAN based vector and, accordingly, they were resistant to kanamycin. The lines V1, V3, S2, S3 and S6 transformed with pGPTV-HPT based vector revealed resistance to hygromycin. Southern analysis of plant DNA digested with one restriction enzyme has shown that about $\frac{1}{10}$ to $\frac{1}{3}$ of the transformed plants have only one copy of the transgene insertion per genome. 5 µg of non-transformed turnip rape control DNA was also digested with the same restriction enzymes and run in the same gels with the samples (Lane C in FIG. 2).

Results of the Preliminary Experiments in Developing the Transformation Method

Explant source plants. One of the critical points of the protocol is the source plant for transformation. The fast growing meristem is situated in the upper internodes of the inflorescence carrying stem before inflorescence elongation and flowering occurs. Segments derived from the upper 20–50 mm long internode are the most compatible for shoot regeneration and Agrobacterium transformation. Their regeneration and transformation capacities sometime achieve 90–100% for individual plants. Good growth status of the plant with dark green firm stem and free from contamination were inevitable prepositions for a successful transformation procedure.

Plant transformation. Three different *A. tumefaciens* strains, namely C58C1, EHA105 and LBA4404 were tested on transformation capacities. C58C1pGV2260 harbors cointegrative vector pHTT and C58C1pGV3850 harbors both cointegrative vector PHTT and binary vector pGPTV-KAN. Strain EHA105 was supplemented with binary vector pGPTV-KAN and LBA4404 with pGPTV-KAN and pGPTV-HPT vectors. UidA (GUS) intron containing reporter gene was cloned from pGUSint into all binary and cointegrative vectors to exclude mistakes during GUS assay by expression of the gene in Agrobacteria. UidA-int gene was placed under CaMV 35S promoter.

Transformation efficiencies of different Agrobacterium strains were measured as proportion of blue inclusions in callus four days after transformation. The results of three transformation experiments, summarised in Table 2, show that strain LBA4404 reveals highest inoculation capacities which in fact varied between 40–90% depending on the individual transformed plant. This strain is almost two times more effective in transformation of turnip rape than C58C1 or EHA105. Based on these results, *A. tumefaciens* strain LBA4404 was used in the transformation protocol of the invention.

TABLE 2

Transformation efficiencies of different *A. tumefaciens* strains

| Agrobacterium strains with helper plasmids | Sisu blue calli/ all calli | % | Valtti blue calli/ all calli | % | Average % |
|---|---|---|---|---|---|
| C58G1pCV2260pHTT | 16/56 | 29 | 19/61 | 31 | 30 |
| C58C1pGV3850pHTT | 23/54 | 43 | 21/64 | 33 | 38 |
| C58C1pGV3850pGPTV | 5/55 | 9 | 7/60 | 12 | 10.5 |
| EHA105pGPTV | 5/61 | 8 | 11/61 | 18 | 13 |
| LBA4404pGPTV | 40/61 | 66 | 33/62 | 53 | 59.5 |

Shoot regeneration. Effects of different hormones on various explants of mature plants of turnip rape were tested in preliminary experiments to achieve sufficient shoot regeneration. Kinetin has similar positive effect on shoot regeneration induction as BAP. Also IAA has an influence on morphogenesis, as does NAA. Both kinetin and IAA were less effective than BAP and NAA (data not shown).

Leaf discs, petiole and inflorescence carrying stem segments, hypocotyls and cotyledons were included in the regeneration tests. Regeneration capacities of hypocotyls as well as inflorescence carrying stem and petiole segments seemed to be better than leaf discs and cotyledons. Two different shoot regeneration strategies were developed for hypocotyl and inflorescence carrying stem segments of turnip rape. The first is shoot induction by cultivation of explants on the same hormone composition throughout the entire transformation procedure, and the second is change of hormone balance from auxins to cytokinins. One step regeneration was the best on 2 mg/l BAP and 0.5 mg/l NAA. Regenerated shoots, however, suffered from vitrification and shoot primordia formed directly on explant surface without callus formation, which decreased the possibility of transgenic tissue selection. Highest average shoot regeneration rate was about 40–60% for inflorescence carrying stem segments.

Two step regeneration was more promising in our experiments. Cultivation on 1.5–0.5 mg/l 2,4-D for 3–6 days (time and concentrations depending on cultivar) and then 1–2 weeks cultivation on 3 mg/l BAP and 0.05 mg/l NAA led to fast growth of callus and green embryo formation. Optimal hormone treatment for different cultivars is shown in Table 3. The best rate of embryo and primordia formation varies within 40–80% for inflorescence carrying stem segments. Embryos with developed primordia and small fragment of callus should be transferred on MS medium without hormones to prevent following vitrification and degradation on hormonal medium. Green nodules and primordia developed into shoots and roots in 2–3 weeks on MS medium without hormones. Recovered shoots often had tendency for inflorescence formation. To overcome this and to induce root formation, recovered shoots and cuttings were cultivated subsequently on MS medium supplemented with 0.2 mg/l NAA. This two step shoot regeneration (from 2,4-D to BAP) seemed to be more advantageous for transformation procedure due to better selection possibility during callus formation step, and subsequently the protocol was used in the transformation procedure of the invention.

TABLE 3

Optimal hormone treatinent for shoot regeneration of inflorescence carrying stem segments of turnip rape cultivars Sisu and Valtti

| Cultivar | Auxin treatment (first step) | Cytokinine treatment, (second step), 1–2 weeks | Shoot formation, hormone free | Rooting, shoot elongation | Selection mg/l Kan | Hyg |
|---|---|---|---|---|---|---|
| Sisu | 1.5D 3 days | 3B + 0.05N | 2–6 weeks | 0–0.2N | 20 | 20 |
| Valtti | 0.5D 6 days | 2B or 3B + 0.05N | 2–6 weeks | 0.1–0.2N | 25 | 20 |

*abbreviations: D—2,4-D; B—BAP; N—NAA, hormone concentrations are given in mg/l.

Many different factors were tested on impact on shoot regeneration efficiency. Optimal parameters were found for pH-5.5–5.6, for sucrose content-2%, solidifiers-0.7% agar. Differences from standard Murashige-Skoog medium proportions of $NH_4^+$, $NO_3^-$, $K^+$ and $Ca^{++}$ ions as well as addition of glucose, or cultivation on B5 medium did not show distinct positive effect on shoot regeneration.

Silver nitrate application and aeration. The use of silver nitrate in in vitro cultivation of turnip rape has often been reported as an essential factor for shoot regeneration (Chi et al. 1990; Hachey et al. 1991; Mukhopadhuay et al. 1992; Radke et al. 1992). Both silver nitrate and use of a porous paper tape for sealing of Petri dishes have been shown to decrease ethylene content and humidity in the culture vessel during cultivation. We have examined the effect of silver nitrate on regeneration capacity of explants of turnip rape. Shoot regeneration optimum was in our experiments between 5–10 mg/l (30–60 μM) $AgNO_3$. We have found 5 mg/l of silver nitrate to be enough for continuous cultivation of stem explants and regeneration of shoots. High concentrations of silver nitrate (10 mg/l and more) can, however, lead to browning and partial necrosis of cultivated calli.

Silver nitrate has negative effect on growth of Agrobacterium. Addition of 5 mg/l (30 μM) of silver nitrate suppresses Agrobacterium growth on MS medium during co-cultivation with plant explants. We have transformed inflorescence stem segments of turnip rape using different concentrations of silver nitrate and sealed plates with plant explants by parafilm or porous paper tape. Transformation efficiency was examined in histological GUS assay 4 days after co-cultivation. Transformation efficiency is shown in Table 4 as proportion of explants with blue inclusions in the calli per all explants (also in %). Silver nitrate in the cultivation medium does not have a negative effect on transformation in our experiments. Apparently, silver nitrate has even positive effect on transformation efficiency. We suppose that inflorescence carrying stem segments are so large that silver nitrate has not a great negative impact on Agrobacterium, if the explant is placed horizontally. Only the down oriented side of an explant is not transformed when silver nitrate is present in the MS medium. Silver nitrate seems to have some positive effect on transformation by increasing viability of the explants through lowering the adverse ethylene impact. This supposition can help to explain results of the experiment shown in Table 4.

Sealing with porous paper tape (e.g. 3M porous paper tape available for medicinal applications) increases aeration and decreases ethylene content in comparison to parafilm. Porous paper tape sealing increases regeneration capacities in our experiments from 0–5% to 60–80% and at least does not have a negative effect on transformation (see Table 4).

TABLE 4

Silver nitrate, acetosyringone and porous paper tape sealing effect on transformation of inflorescence stem segments of turnip rape plants by Agrobacterium LBA4404pGPTV-KAN-GUSint.

| Factors of cultivation | cv. Sisu GUS +/all | % | cv. Valtti GUS +/all | % | Average % |
|---|---|---|---|---|---|
| 0 mg/l $AgNO_3$ | 17/58 | 29.3 | 20/61 | 32.8 | 31.5 |
| 5 mg/l $AgNO_3$ | 19/70 | 27.1 | 14/37 | 37.8 | 29.5 |
| 10 mg/l $AgNO_3$ | 15/53 | 28.3 | 15/32 | 46.9 | 37.6 |
| 15 mg/l $AgNO_3$ | 17/40 | 42.5 | 14/43 | 32.6 | 37.6 |
| 0 μM AS* | 28/65 | 43.1 | 27/72 | 37.5 | 40.3 |
| 100 μM AS** | 24/65 | 36.9 | 36/78 | 46.2 | 41.6 |
| 100 μM AS*** | 29/65 | 44.6 | 35/72 | 48.6 | 46.6 |
| parafilm sealed | 6/24 | 25 | 6/10 | 60 | 42.5 |
| paper tape sealed | 13/21 | 61.9 | 7/12 | 58.3 | 60.1 |

*AS means acetosyringone added in YEB Agrobacterium growth meduim.
**AS was added in MS medium during inoculation and cocultivation with Agrobacterium.
***AS was added in MS medium and Agrobacterium was grown one night with addition of 100 μM acetosyringone.

Selection. To prevent Agrobacterium growth on the medium we used claforan (cefotaxim) 500 mg/l or carbenicillin 200 mg/l. Claforan, however, decreased shoot regeneration frequency 2–5 times compared to carbenicillin, which does not have an apparent negative effect on regeneration (data not shown). This negative effect of claforan leads to full block of recovering of transgenic shoots after inoculation with Agrobacteria. Therefore we use carbenicillin in the transformation procedure according to the invention.

Using nptII and hpt genes in transformation constructions provides the plants resistance to kanamycin and hygromycin, respectively. It was found in preliminary experiments that 10–15 mg/l of each of these antibiotics prevent morfogenesis of explants. Because morfogenesis occurs mainly on the basal side of the stem segmets, explants are placed basal side down on the selection medium. It makes selection more effective and sufficiently decreases proportion of non-transgenic escapes. We have found that selection should be applied immediately after washing of Agrobacteria from plant explants. First green regenerative nodules form on the calli 7–10 days after cutting of stem segments, and selection of transformed tissues should be performed before that. We have not obtained any transformed shoots when we start selection later than immediately after co-cultivation.

Selection of transformed tissue on 10 mg/l of either of the antibiotics was not enough and all green regenerated shoots did not show GUS expression. Concentrations of 20–25 mg/l were optimal for selection. Results of regeneration experiments of transgenic shoots under selection on 20 mg/l kanamycin or hygromycin are presented in Table 5. Turnip rape plants cv. Valtti and Sisu were transformed with LBA4404 pGPTV-KAN-GUSint and LBA4404 pGPTV-HPT-GUSint. Based on results of our experiments, we have found that selection on hygromycin was more preferable because the escape proportion was about 10% for hygromycin and 80–90% for kanamycin. Both antibiotics in concentration 40–50 mg/l have a negative impact on regeneration of transgenic shoots. Stem segments died in a few weeks and transgenic calli did not produce shoots. Consequently, hygromycin and kanamycin were used in transformation in concentration 20–25 mg/l.

sterilized water. Excess water was removed by placing the explant on sterilized filter paper.

The damaged upper and bottom surfaces were cut out. The internodes were cut in 4 to 8 mm segments which were placed in a horizontal position onto MS agar plates (see Materials and Methods) containing 30 $\mu$M (5 mg/l) AgNO$_3$, 3 mg/l 2,4-D and 100 $\mu$M acetosyringone. The plates with the stem explants were sealed with 3M porous paper tape, and cultivated for 24 hours.

*Agrobacterium tumefaciens* strain LBA4404 with a helper plasmid pLA4404 and a binary plasmid PGPTV-HPT harboring uidA (GUS) intron containing gene under the control of CaMV 35S promoter was grown on YEB agar plate. Agrobacterium cells taken from one colony were inoculated into YEB broth supplemented with 25 mg/l rifampicin and 50 mg/l kanamycin, and agitated overnight at +28° C. The Agrobacterium cell culture so obtained was inoculated into fresh YEB broth in the proportion of 1/100 (v/v) and grown for another night on the shaker at +28° C. The YEB broth contained the same antibiotics as the previous culture medium and was supplemented with 100 $\mu$M of acetosyringone. The cell culture so obtained was used for transformation of plants.

Liquid MS medium without sucrose was inoculated with 1/10 (v/v) of the Agrobacterium culture obtained above and the turnip rape stem segment explants cultured for 24 hours were immersed therein. After 1 to 3 minutes the explants were placed onto sterilized filter paper to remove extra liquid from the explant surface.

The explants were placed in a vertical position, basal side down onto MS agar plates containing 30 $\mu$M (5 mg/l) of silver nitrate, 3 mg/l of BAP, 0,05 mg/l of NAA, 200 mg/l of carbenicillin and 20 mg/l of hygromycin for selection of

TABLE 5

Transgenic shoot regeneration frequency in two different selective systems (cultivars Sisu and Valtti)

| Selection | Green shoots per all explants | % | GUS positive per all explants | % | Escapes per green shoots | % |
|---|---|---|---|---|---|---|
| Kanamycin | 59/182 | 32 | 7/182 | 4 | 52/59 | 88 |
| Hygromycin | 13/131 | 10 | 12/131 | 9 | 1/13 | 8 |

Analysis of transformation. Green regenerated shoots were checked for GUS activity. Leaves or leaf pieces were prepared for histological GUS assay as described above.

The following example illustrates an advantageous transformation protocol for turnip rape cultivar Sisu.

EXAMPLE 1

Transformation Protocol for Turnip Rape (*Brassica Rapa* var. *Oleifera*, syn. *B. Campestris*) cv. Sisu with *Agrobacterium Tumefaciens* Strain LBA4404 Harboring Binary Plasmid pGPTV-HPT with UidA Intron Containing Gene Turnip rape plants were grown in greenhouse conditions for about 1 month. Before the stage of inflorescence elongation and opening of the first flowers the two upper internodes of the inflorescence carrying stem were excised. The internodes were sterilized for 90 sec. in 70% ethanol and 10 min. in Na-hypochlorite (2% active Cl$^-$) with addition of 1 to 3 drops of Tween-20, and washed 3 times in transgenic tissues and induction of shoot regeneration, for 1 to 2 weeks. In case cultivation times over 10 days were used, the plates were changed into fresh ones. The plates were sealed by 3M porous paper tape.

The explants were placed in vertical position, basal side down onto MS agar plates containing 30 $\mu$M (5 mg/l) of silver nitrate, 3 mg/l of BAP, 0,05 mg/l of NAA, 200 mg/l of carbenicillin and 20 mg/l of hygromycin for selection of transgenic tissues and induction of shoot regeneration, for 1 to 2 weeks. In case cultivation times over 10 days were used, the plates were changed into fresh ones. The plates were sealed by 3M porous paper tape.

Formation of green regenerative nodules or primordia was monitored, and whole explants or pieces of callus with re-generated green nodules and primordia were placed onto MS agar plates without hormones, supplemented with 30 $\mu$M (5 mg/l) of silver nitrate, 200 mg/l of carbenicillin and 20 mg/l of hygromycin. In 2 to 6 weeks the green nodules and primordia regenerated into transgenic green shoots.

Developed transgenic shoots were grown on the same medium with silver nitrate content lowered to 15 $\mu$M (2.5 mg/l). In case the shoots did not form roots or an inflorescence, they were cut and cuttings were placed on MS agar containing 0.2 mg/l of NAA, 15 µM (2.5 mg/l) of silver nitrate, 200 mg/l of carbenicillin but no hygromycin. The culture vessels were always sealed with the 3M porous paper tape. Turnip rape plants were propagated in vitro on the same MS agar medium.

Rooted transgenic plants were tested for transformation by histological GUS assay and transferred in soil in greenhouse conditions. About 5 g of the plants grown on greenhouse was used for DNA isolation for Southern analysis (see FIG. 2).

References

Becker D., Elke K., Schell J., Masterson R. (1992) New plant binary vectors with selectable markers located proximal to the left T-DNA border. Plant Mol. Biol. 20: 1195–1197.

Chi G.-L., Barfield D. G., Sim G.-E., Pua E.-C. (1990) Effect of $AgNO_3$ and aminoethoxyvinylglycine on in vitro shoot and root organogenesis from seedling explants of recalcitrant Brassica genotypes. Plant Cell Reports 9: 195–198

Datla R. S. S., Bekkaoui F., Hammerlind J. K., Pilate G., Dunstan D. J., Crosby W. L. (1993) Improved high-level constitutive foreign gene expression in plants using an AMV RNA4 untranslated leader sequence. Plant. Sci., 94: 139–149

Deblaere R., Bytebier B., De Greve H., Deboeck F., Shell J., Van Montagu M., Leemans J. (1985) Efficient octopine Ti plasmid—derived vectors for Agrobacterium-mediated gene transfer to plants. Nucl. Acids Res. 13: 4777–4788

Elomaa P., Honkanen J., Puska R., Seppanen P, Helariutta Y., Mehto M., Kotilainen M., Nevalainen L., Teeri T. H. (1993) Agrobacterium-mediated transfer of antisense chalcone synthase cDNA to Gerbera Hybrida inhibits flower pigmentation. Bio/Technol. 11: 508–511

Fry J., Barnason A., Horsch R. B. (1987) Transformation of Brassica napus with *Agrobacterium tumefaciens* based vectors. Plant Cell Reports 6: 321–325

Hachey J. E., Sharma K. K., Moloney M. M. (1991) Efficient shoot regeneration of Brassica campestris using cotyledon explants cultured in vitro. Plant Cell Reports, 9: 549–554

Hoekema A., Hirsch P. R., Hooykaas P. J. J., Schilperoort R. A. (1983) A binary plant vector strategy based on separation of vir and T-region of the A. tumefaciens Ti-plasmid. Nature (London) 303: 179–180

Hood E. E., Gelvin S. B., Melchers L. S., Hoekema A. (1993) New Agrobacterium helper plasmid for gene transfer to plants. Transgenic research 2: 208–218

Knutzon D. S., Thompson G. A., Radke S. E., Johnson W. B., Knauf V. C., Kridl J. C. (1992) Modification of Brassica seed oil by antisense expression of a stearol-acyl carrier protein desaturase gene. Proc. Natl. Acad. Sci. USA 89: 2624–2628

Lihtenstain C., Draper J. (1985) Gene engineering of plants. In: DNA cloning—a practical approach. v. 2, part 4, ed. Glover D. M., IRL Press.

Mukhopadhyay A., Arumugam N., Nandakumar P. B. A., Pradhan A. K., Gupta V., Pental D. (1992) Agrobacterium mediated genetic transformation of oilseed Brassica campestris: Transformation frequency is strongly influenced by the mode of shoot regeneration. Plant Cell Reports 11: 506–551

Murashige T., Skoog F. (1962) A revised medium for rapid growth and bioassay with tobacco tissue culture. Physiol. Plant. 15: 472–493

Palmer C. E. Enhanced shoot regeneration from *Brassica campestris* by silver nitrate. Plant Cell Reports 11: 541–545

Pua E. C., Mehra-Palta A., Nagy F., Chua N. H. (1987) Transgenic plants of *Brassica napus L*. Bio/Technology 5: 815–817

Radke S. E., Andrews B. M., Moloney M. M., Crouch M. L., Kridl J. C., Knauf V. C. (1988) Transformation of *Brassica napus L*. using *Agrobacterium tumefaciens*: developmentally regulated expression of a reintroduced napin gene. Theor. Appl. Genet. 75: 685–694

Radke S. E., Turner J. C., Facciotti D. (1992) Transformation and regeneration of *Brassica rapa* using *Agrobacterium tumefaciens*. Plant Cell Reports 11: 499–505

Shiba H., Hinata K., Suzuki A., Isogai A. (1995) Breakdown of self-incompatibility in Brassica by the antisense RNA of the SLG gene. Proc. Japan Acad. 71, Ser. B: 81–83

Vancanneyt G., Schmidt R., O'Connor-Sanchez A., Willinitzer L., Rocha-Sosa M. (1990) Construction of an intron-containing marker gene: Splicing of the intron in transgenic plants and its use in monitoring early events in Agrobacterium-mediated plant transformation. Mol. Gen. Genet. 220: 245–250.

Zambryski P., Joos H., Genetello C., Leemans J., Van Montagu M., Shell J. (1983) Ti plasmid vector for the introduction of DNA into plant cells without alteration of their normal regeneration capacity. EMBO J. 2: 2143–2150

What is claimed is:

1. A method for transforming mature plants of turnip rape, comprising
   (i) excising an internode section of the inflorescence-carrying stem of a mature turnip rape plant,
   (ii) sterilizing said internode section, and cutting it in 4–8 mm segments to obtain an internode segment,
   (iii) placing an internode segment in a horizontal position on an agar pre-cultivation medium supplemented with 15–90 µM of silver nitrate and 2,4-dichlorophenoxyacetic acid (2,4-D) hormone,
   (iv) pre-cultivating the internode segment on said medium for 1 day,
   (v) immersing the internode segment in a MS solution inoculated with *Agrobacterium tumefaciens* bacteria carrying at least one gene heterologous to said turnip rape,
   (vi) placing the immersed internode segment in a horizontal position on an agar MS co-cultivation medium,
   (vii) co-cultivating the internode segment with Agrobacteria for 2 days,
   (viii) washing the internode segment to remove the Agrobacteria,
   (ix) placing the internode segment in a vertical position with the basal side down on MS agar medium for selection with an antibiotic, the medium being supplemented with cytokinine hormones and silver nitrate, to obtain an internode segment with regenerated primordia or embryonic green nodules,
   (x) placing the internode segment with regenerated primordia or embryogenic green nodules on a hormone-free regeneration medium, and
   (xi) recovering the transgenic shoots regenerated.

2. The method according to claim 1, wherein the selection medium used in step (ix) contains carbenicillin for the removal of Agrobacterium contamination.

3. The method according to claim 1, wherein agar media are present in plates and said plates are sealed by porous paper tape to achieve extra aeration.

4. The method according to claim 1, wherein the internode section of the inflorescence-carrying stem is a section cut from the upper 2 to 5 cm portion of the inflorescence-carrying stem containing one-to-two internodes.

5. The method according to claim 1, wherein the medium in the pre-cultivation step (iv) and selection step (ix) is a 0.7% agar MS medium with 2–3% sucrose.

6. The method according to claim 1, wherein the concentration of 2,4-dichlorophenoxyacetic acid in the pre-cultivation and co-cultivation media is from 0.5–1.5 mg/l.

7. The method according to claim 1, wherein in step (i), the concentration of 2,4 D is from 0.5–1.5 mg/L, and the cultivation step is performed for 1 to 2 weeks on a medium containing at least one cytokine to initiate shoot regeneration.

8. The method of claim 1, in which the silver nitrate concentration in the pre-cultivation and selection media is in the range from 30 to 90 $\mu$M.

9. The method of claim 1, in which the silver nitrate concentration in the pre-cultivation and selection media is in the range from 30 to 60 $\mu$M.

10. The method of claim 1, in which the cytokine hormones in step (ix) is a mixture of 6-benzylaminopurine and $\alpha$-naphthaleneacetic acid.

11. The method of claim 10, in which 6-benzylaminopurine is present at a concentration of 2–3 mg/L and $\alpha$-naphthaleneacetic acid is present at a concentration up to 0.05 mg/L.

12. The method of claim 1, in which the antibiotic in step (ix) is kanamycin or hygromycin.

13. The method of claim 1, in which the antibiotic in step (ix) is hygromycin.

14. The method of claim 10, in which the antibiotic in step (ix) is kanamycin or hygromycin.

15. The method of claim 11, in which the antibiotic in step (ix) is kanamycin or hygromycin.

* * * * *